Figure 1:
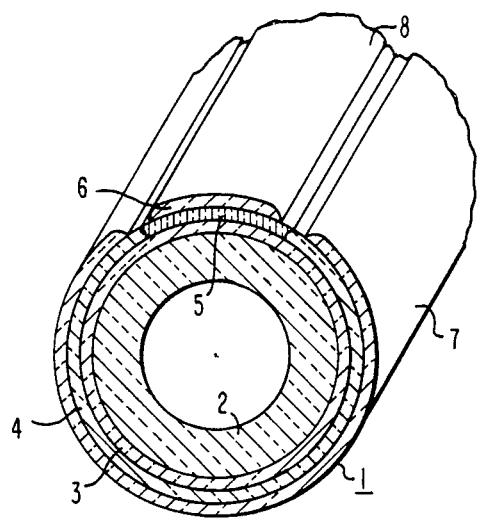

United States Patent [19]

Ruka

[11] Patent Number: 4,562,124
[45] Date of Patent: Dec. 31, 1985

[54] AIR ELECTRODE MATERIAL FOR HIGH TEMPERATURE ELECTROCHEMICAL CELLS

[75] Inventor: Roswell J. Ruka, Churchill Boro, Pa.

[73] Assignee: Westinghouse Electric Corp., Pittsburgh, Pa.

[21] Appl. No.: 693,903

[22] Filed: Jan. 22, 1985

[51] Int. Cl.$^4$ .............................................. H01M 8/12
[52] U.S. Cl. ........................................ 429/30; 429/31; 429/193; 429/33; 501/152; 252/519; 252/521
[58] Field of Search ...................... 429/30, 31, 32, 191, 429/193, 101, 103; 252/519, 521, 62.3 R; 204/291, 421; 501/152; 420/900; 423/155, 596, 599

[56] References Cited

U.S. PATENT DOCUMENTS

| | | |
|---|---|---|
| 3,400,054 | 9/1968 | Ruka et al. . |
| 3,430,536 | 11/1969 | Arthur ............................ 252/521 X |
| 3,834,943 | 9/1974 | van den Berghe et al. . |
| 4,052,532 | 10/1977 | Tannenberger et al. ............. 429/33 |
| 4,133,778 | 1/1979 | Gray ................................. 252/517 |
| 4,174,260 | 11/1979 | Schmidberger .................. 429/31 X |
| 4,330,633 | 5/1982 | Yoshisato et al. .................. 501/152 |
| 4,490,444 | 12/1984 | Isenberg ............................ 429/31 |

FOREIGN PATENT DOCUMENTS 2315151 1/1977 France .

*Primary Examiner*—Anthony Skapars
*Attorney, Agent, or Firm*—R. D. Fuerle

[57] ABSTRACT

Disclosed is a solid solution with a perovskite-like crystal structure having the general formula $$La_{1-x-w}(M_L)_x(Ce)_w(M_{S1})_{1-y}(M_{S2})_yO_3$$

where $M_L$ is Ca, Sr, Ba, or mixtures thereof, $M_{S1}$ is Mn, Cr, or mixtures thereof and $M_{S2}$ is Ni, Fe, Co, Ti, Al, In, Sn, Mg, Y, Nb, Ta, or mixtures thereof, w is about 0.05 to about 0.25, x+w is about 0.1 to about 0.7, and y is 0 to about 0.5. In the formula, $M_L$ is preferably Ca, w is preferably 0.1 to 0.2, x+w is preferably 0.4 to 0.7, and y is preferably 0. The solid solution can be used in an electrochemical cell where it more closely matches the thermal expansion characteristics of the support tube and electrolyte of the cell.

13 Claims, 3 Drawing Figures

AIR ELECTRODE MATERIAL FOR HIGH TEMPERATURE ELECTROCHEMICAL CELLS

GOVERNMENT CONTRACT

The Government of the United States of America has rights in this invention pursuant to Contract No. DE-AC0280-ET17089, awarded by the U.S. Department of Energy.

BACKGROUND OF THE INVENTION

Lanthanum manganite, modified by substitution of calcium or strontium ions for part of the lanthanum, is used as an electrode material for high temperature solid electrolyte fuel cells. Lanthanum chromite, also modified by substitution of calcium or strontium ions for part of the lanthanum, has been considered for use as an air electrode, or as both an air electrode and a support material for high temperature solid electrolyte fuel cells. These fuel cells are made of successive layers of bonded ceramic materials which perform the functions of support, air electrode, electrolyte, fuel electrode, interconnection, and other functions. In order that the fuel cells remain undamaged during thermal cycling between the high temperatures of fabrication or operation, and room temperature, it is desirable to match the thermal expansion characteristics of the various layers that make up the fuel cells. If the various layers are mismatched in thermal expansion characteristics, the layers can crack during thermal cycling and render the fuel cell ineffective or at least less effective.

A difficulty in constructing the fuel cells using the modified lanthanum manganite and modified lanthanum chromite is that these materials, modified to have the highest electrical conductivity, have a higher coefficient of thermal expansion than do some other materials typically used in making the fuel cell, such as those used in the stabilized zirconia electrolyte or the stabilized zirconia support tube. While the coefficients of thermal expansion of the various materials depend on the exact composition selected for a particular fuel cell, it would be highly desirable to be able to adjust the coefficients of thermal expansion of lanthanum manganite and lanthanum chromite to match the coefficients of thermal expansion of the other materials. In this way, these materials could be used in fuel cells without cracking of any of the cell components during thermal cycling.

SUMMARY OF THE INVENTION

I have discovered that if a small amount of the lanthanum in the modified lanthanum manganite or the modified lanthanum chromite is replaced by cerium, the coefficient of thermal expansion is reduced so that it now more precisely matches the coefficient of thermal expansion of other materials such as those used in the support tube and the electrolyte of the fuel cell. This wall a surprising discovery because cerium is only one of fourteen rare earth compounds, which have many chemical similarities, yet cerium was the only rare earth additive which I tested which, at comparable concentrations, has such a large effect on the coefficient of thermal expansion of modified lanthanum chromite and modified lanthanum manganite. The replacement of a small amount of lanthanum by cerium in these compounds gives a small increase in resistivity, but this is small enough so that it is still a very useful air electrode material.

DESCRIPTION OF THE INVENTION

Figure 2:
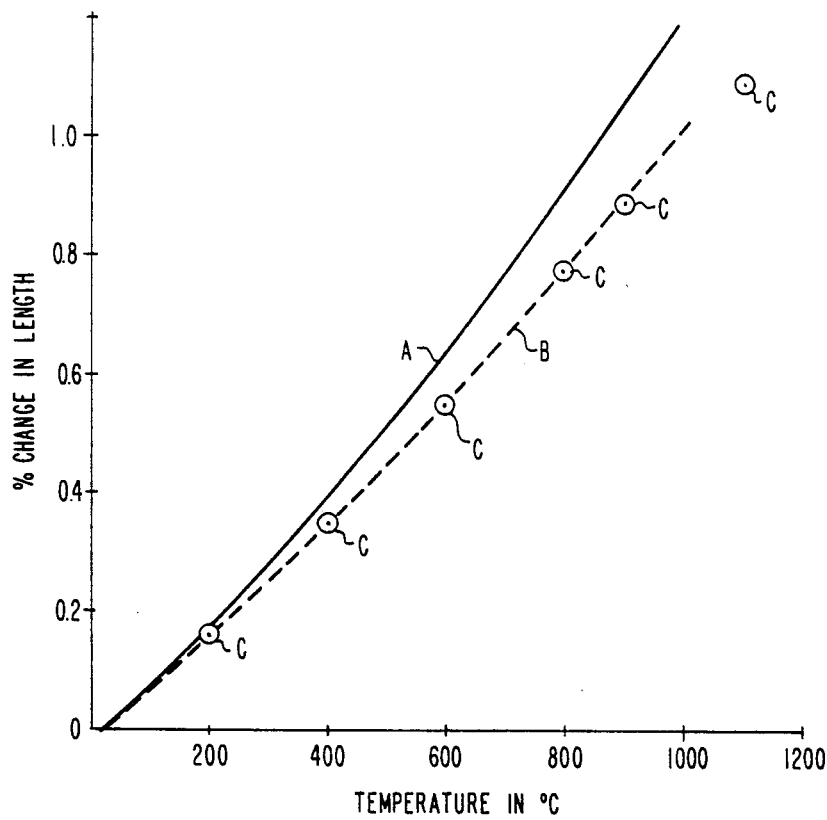
Figure 3:
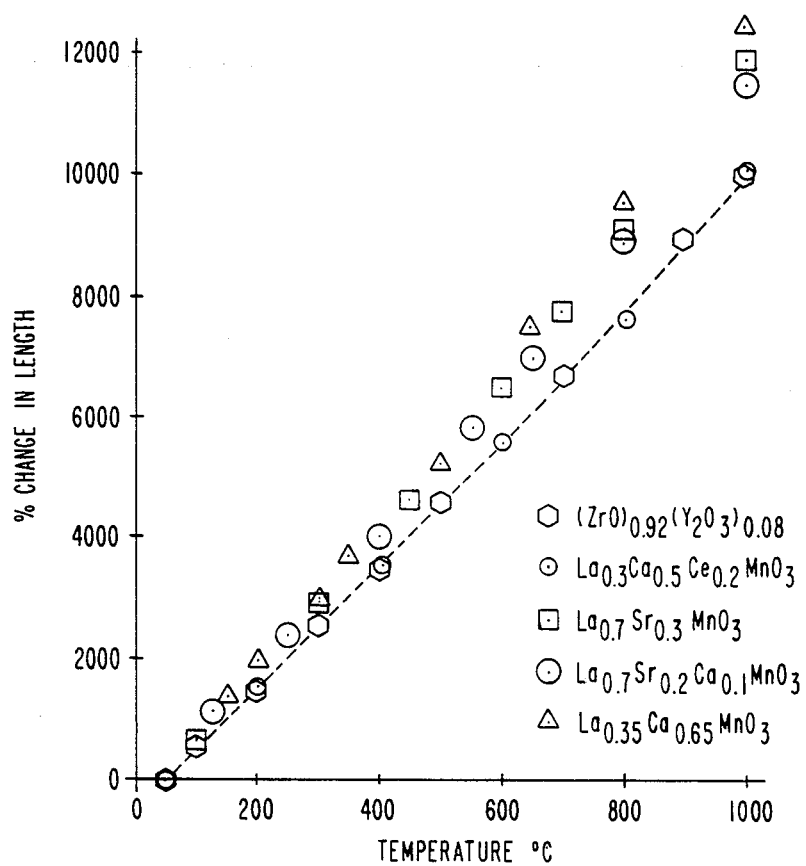

FIG. 1 is a schematic view in section of a certain presently preferred embodiment of a fuel cell according to this invention; and FIGS. 2 and 3 are graphs giving the thermal expansion of various materials prepared in the example.

In FIG. 1, fuel cell 1 has a support tube 2 which provides structural integrity to the cell. The support tube is typically comprised of calcia stabilized zirconia forming a wall porous to gas permeation, approximately 1 to 2 mm thick. Surrounding the outer periphery of the support tube 2 is a thin porous air electrode or cathode 3. The cathode 3 is typically a composite oxide structure approximately 15 microns to 1,000 microns thick which is deposited onto the support tube through well-known techniques such as plasma spraying, or spraying or dipping in a slurry followed by sintering. The air electrode may be a chemically modified oxide or mixture of oxides including lanthanum manganite or lanthanum chromite. Over the electrode is a gas-tight solid electrolyte 4, typically yttria stabilized zirconia, about 1 micron to about 100 microns thick. A selected longitudinal segment 5 is masked during deposition of the electrolyte and an interconnect material 6 is deposited on segment 5. The interconnect material 6 must be electrically conductive in both an oxygen and fuel environment. The interconnect is about 5 to about 100 microns thick and is typically made of lanthanum chromite doped with calcium, strontium, or magnesium. Surrounding the remainder of the cell except for the interconnect area is a fuel electrode 7 which functions as the anode. A typical anode is about 30 to 100 microns thick. A material 8, which is of the same composition as the anode, is also deposited over the interconnect 6. This material is typically nickel zirconia or cobalt zirconia cermet and is about 50 to 100 microns thick.

In operation, a gaseous fuel, such as hydrogen or carbon monoxide, is directed over the outside of the cell, and a source of oxygen passes through the inside of the cell. The oxygen source forms oxygen ions at the electrode-electrolyte interface which migrate through the electrolyte material to the anode while electrons are collected at the cathode, thus generating a flow of electrical current in an external load circuit. A number of cells can be connected in series by contact between the interconnect of one cell and the anode of another cell. A more complete description of the operation of this type of fuel cell generator can be found in U.S. Pat. Nos. 4,395,468 and 3,400,054, and in a patent application filed by A. O. Isenberg, Ser. No. 323,641, filed Nov. 20, 1981, herein incorporated by reference.

The ceramic of this invention is a solid solution having a perovskite-like crystal structure, and falls within the general formula $La_{1-x-w}(M_L)_x(Ce)_w(M_{S1})_{1-y}(M_{S2})_yO_3$. The perovskite structure has an $ABO_3$ chemical composition where the $M_{S1}$ and $M_{S2}$ atoms are the smaller B ions of the structure, and the lanthanum, $M_L$, and Ce are the larger A ions of the structure. In the general formula, $M_L$ is calcium, strontium, barium, or a mixture thereof, and is preferably 100 mole% calcium as it is inexpensive and it has been found to work well in solid oxide fuel cells. These ions are present to improve the electrical conductivity. In the formula, $M_{S1}$ is manganese, chromium, or a mixture thereof, and $M_{S2}$ is nickel, iron, cobalt, titanium, aluminum, indium, tin, magnesium, yttrium, niobium, tantalum, or mixtures thereof. In the formula, y is 0 to about 0.5 and is preferably 0, as the addition of other compounds for some of the manganese or chromium is usually not beneficial. Manganese in the compound is used for good electrical conductivity. Chromium in the compound reduces electrical conductivity but does not interact as much with the electrolyte as the manganese does. Moreover, none of these elements should be added in excess of their solubility limit. The value of x+w is about 0.1 to about 0.7, and is preferably about 0.4 to about 0.7, as at lower values the conductivity falls off and at higher values the ceramic has poor thermal expansion behavior and may have phase changes. The value of w is about 0.05 to about 0.25, and is preferably about 0.1 to about 0.2, as less does not significantly diminish the thermal expansion of the ceramic and more lowers the conductivity of the ceramic and is not needed to match the thermal expansion range of the stabilized zirconia materials, such as $(ZrO_2)_{0.85}(CaO)_{0.15}$, being used in such electrochemical cells.

Certain combinations of materials have been experimentally found to have coefficients of thermal expansion which are well matched, thus these materials can be bonded together with less danger of cracks occurring during thermal cycling. Examples include an electrolyte of $(ZrO_2)_{0.9}(Y_2O_3)_{0.1}$ and an electrode of $La_{0.3}Ca_{0.5-0.6}Ce_{0.2-0.1}MnO_3$. Another example is a support tube of $(ZrO_2)_{0.85}(CaO)_{0.15}$ with an electrode of $La_{0.3}Ca_{0.5-0.6}Ce_{0.2-0.1}MnO_3$. Another example is an electrolyte of $(ZrO_2)_{0.9}(Y_2O_3)_{0.1}$ in combination with an electrode of $La_{0.3}Ca_{0.5-0.6}Ce_{0.2-0.1}CrO_3$. Still another example is a support or electrolyte of $(ZrO_2)_{0.85}(CaO)_{0.15}$ in combination with an electrode of $La_{0.3}Ca_{0.5-0.6}Ce_{0.2-0.1}CrO_3$.

The modified lanthanum manganite or lanthanum chromite materials are solid solutions which consist of a single phase—they are not mechanical mixtures consisting of two phases. These ceramics can be prepared by mixing compounds of the elements required in the proportions specified, followed by pressing and sintering at 1400° to 1800° C. for about 1 to 4 hours. These compounds include oxides, carbonates, and other compounds that form oxides upon heating, such as oxalates. For use as a combination support tube and electrode for a solid electrolyte electrochemical cell, particle size and sintering temperature are selected to give a density of the sintered oxide that does not exceed about 80% of theoretical, to permit surrounding gases to permeate to the electrode-electrolyte interface, where electrochemical reactions occur. In addition to being used in a solid electrolyte electrochemical cell such as a fuel cell, an electrolytic cell, or oxygen gauge, the lanthanum chromite solid solutions of this invention can also be used to improve the thermal expansion match between electrode components in magnetohydrodynamic (MHD) generators.

The following examples further illustrate this invention.

EXAMPLE

Using the compounds $MnO_2$, $Cr_2O_3$, $La_2O_3$, $CaCO_3$, $SrCO_3$, $CeO_2$, and $Y_2O_3$, perovskite-like solid solutions having the compositions $La_{0.3}Ca_{0.5}Ce_{0.2}MnO_3$, $La_{0.7}Sr_{0.3}MnO_3$, $La_{0.7}Sr_{0.2}Ca_{0.1}MnO_3$, $La_{0.35}Ca_{0.65}MnO_3$, $La_{0.5}Ca_{0.5}CrO_3$, and $La_{0.3}Ca_{0.5}Ce_{0.2}CrO_3$ were prepared by mixing the compounds in the necessary proportions and pressing under 1,000 to 10,000 psi followed by sintering for 1 to 4 hours. The sintering was conducted at 1400° to 1500° C. for the manganese containing compounds and at about 1600° C. for the chromium containing compounds. Sintered bars of $(ZrO_2)_{0.92}(Y_2O_3)_{0.8}$ were also prepared for comparison of the thermal expansion data. The products were rectangular bars about 1 inch long and about ¼ inch × about ¼ inch thick. The bars were trimmed, then heat cycled between 1350° C. and room temperature three times in order to stabilize their thermal expansion characteristics.

The expansion of the bars as the temperature increased was then measured. FIGS. 2 and 3 give the results. In FIG. 2, A is $La_{0.5}Ca_{0.5}CrO_3$, B is $(ZrO_2)_{0.92}(Y_2O_3)_{0.08}$, and C is $La_{0.3}Ca_{0.5}Ce_{0.2}CrO_3$. FIGS. 2 and 3 show that the cerium containing compounds matched the thermal expansion characteristics of the yttria stabilized zirconia much better than did similar compounds which did not contain cerium.

I claim:

1. A compound comprising a solid solution having the general formula

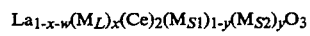

$$La_{1-x-w}(M_L)_x(Ce)_2(M_{S1})_{1-y}(M_{S2})_yO_3$$

where $M_L$ is selected from the group consisting of Ca, Sr, Ba, and mixtures thereof, $M_{S1}$ is selected from the group consisting of Mn, Cr, and mixtures thereof, $M_{S2}$ is selected from the group consisting of Ni, Fe, Co, Ti, Al, In, Sn, Mg, Y, Nb, Ta, and mixtures thereof, w is about 0.05 to about 0.25, x+w is about 0.1 to about 0.7, and y is 0 to about 0.5, but not exceeding the solubility limit.

2. A compound according to claim 1 wherein $M_L$ is Ca and $M_S$ is selected from the group consisting of 100 mole% Mn, Cr, and mixtures thereof.

3. A compound according to claim 1 wherein w is about 0.1 to about 0.2.

4. A compound according to claim 1 wherein x+w is about 0.4 to about 0.7.

5. A compound according to claim 1 wherein the composition of said solid solution is selected to match the thermal expansion characteristics of a stabilized zirconia electrolyte or electrochemical cell support tube.

6. A compound according to claim 1 having the formula $La_{0.3}Ca_{0.5\ to\ 0.6}Ce_{0.2\ to\ 0.1}MnO_3$ bonded to a solid solution having the approximate formula $(ZrO_2)_{0.9}(Y_2O_3)_{0.1}$.

7. A compound according to claim 1 having the formula $La_{0.3}Ca_{0.5\ to\ 0.6}Ce_{0.2\ to\ 0.1}MnO_3$ bonded to a solid solution having the approximate formula $(ZrO_2)_{0.85}(CaO)_{0.15}$.

8. A compound according to claim 1 having the formula $La_{0.3}Ca_{0.5\ to\ 0.6}Ce_{0.2\ to\ 0.1}CrO_3$ bonded to a solid solution having the approximate formula $(ZrO_2)_{0.9}(Y_2O_3)_{0.1}$.

9. A compound according to claim 1 having the formula $La_{0.3}Ca_{0.5\ to\ 0.6}Ce_{0.2\ to\ 0.1}CrO_3$ bonded to a solid solution having the approximate formula $(ZrO_2)_{0.85}(CaO)_{0.15}$.

10. A combination support tube and electrode comprising a compound according to claim 1 in the shape of a tube that is porous to gases, where the density of said solid solution does not exceed about 80% of theoretical.

11. In an electrochemical cell, an electrode or electrode current carrier comprising a compound according to claim 1, bonded to an electrolyte, and which may provide mechanical support for other cell members or a components of the cell.

12. An electrode material in a fuel cell, an electrolytic cell, or an oxygen gauge comprising a compound according to claim 1.

13. A compound comprising a solid solution having the general formula $$La_{1-x-w}(Ca)_x(Ce)_w M_S O_3$$

where $M_S$ is selected from the group consisting of Mn, Cr, and mixtures thereof, w is about 0.1 to about 0.2, and x+w is about 0.4 to about 0.7.

* * * * *

UNITED STATES PATENT AND TRADEMARK OFFICE
CERTIFICATE OF CORRECTION

PATENT NO. : 4,562,124
DATED : December 31, 1985
INVENTOR(S) : Roswell J. Ruka

It is certified that error appears in the above—identified patent and that said Letters Patent is hereby corrected as shown below:

Claim 1, line 3, change the formula to $La_{1-x-w}(M_L)_x(Ce)_w(M_{s1})_{1-y}(M_{s2})_y O_3$ Signed and Sealed this Eighteenth Day of August, 1987

*Attest:*

DONALD J. QUIGG

*Attesting Officer*     *Commissioner of Patents and Trademarks*